United States Patent [19]

Müller et al.

[11] 4,375,560
[45] Mar. 1, 1983

[54] PROCESS FOR THE PREPARATION OF 3,5-DIMETHYLANILINE (SYM. M-XYLIDINE)

[75] Inventors: Werner H. Müller, Eppstein; Rüdiger Berthold, Bad Soden am Taunus, both of Fed. Rep. of Germany

[73] Assignee: Hoechst Aktiengesellschaft, Frankfurt am Main, Fed. Rep. of Germany

[21] Appl. No.: 318,115

[22] Filed: Nov. 4, 1981

[30] Foreign Application Priority Data

Nov. 6, 1980 [DE] Fed. Rep. of Germany ....... 3041848

[51] Int. Cl.³ .............................................. C07C 85/11
[52] U.S. Cl. .................................................... 564/415
[58] Field of Search ........................................ 564/415

[56] References Cited

U.S. PATENT DOCUMENTS 3,255,248 6/1966 Suessenguth et al. .......... 564/415 X
4,247,479 1/1981 Berthold ...................... 564/415 UX

FOREIGN PATENT DOCUMENTS 2623174 12/1977 Fed. Rep. of Germany ...... 564/415

Primary Examiner—Paul F. Shaver
Attorney, Agent, or Firm—Curtis, Morris & Safford

[57] ABSTRACT

The invention provides a process for the preparation of 3,5-dimethylaniline by catalytically dehydrogenating 3,5-dimethyl-cyclohexenone oxime in the gaseous phase. The catalyst contains at least one noble metal of the 8th subgroup of the Periodic Table.

3 Claims, No Drawings

PROCESS FOR THE PREPARATION OF 3,5-DIMETHYLANILINE (SYM. M-XYLIDINE)

Subject of the present invention is a process for the preparation of 3,5-dimethylaniline by catalytic dehydrogenation of 3,5-dimethyl-cyclohexenone oxime in the gaseous phase.

3,5-Dimethylaniline is an intermediate for the manufacture of dyestuffs, and can be used as diazo component for azo dyes or as condensation component for pigment dyestuffs of the perylene-tetracarboxylic acid series.

Hitherto, 3,5-dimethylaniline has been prepared by reaction of sym. m-xylenol with ammonia at elevated temperature and pressure. This process requires much technological and apparatus expenditure, and as starting material sym. m-xylenol obtained from bituminous coal tar. Moreover, this xylenol is not completely free from isomers.

It was therefore the object of the present invention to find a method of preparing 3,5-dimethylaniline which is independent of sym. m-xylenol.

It is known (Krauch, Kunz: Reaktionen der organischen Chemie, 5th ed., Heidelberg 1976, p. 585) that oximes of determined alicyclic ketones can be converted to the corresponding acetanilides by means of acetic anhydride and sulfuric or hydrochloric acid. By saponification with alkali metal hydroxides, the intended aromatic amines are obtained from these acetanilides. However, this method is very complicated and causes considerable environmental strain because of the inevitably formed alkali metal salts.

Attempts made by E. C. Horning et al. (J.Am.Chem.Soc. 69, 1907 (1947)) to convert 3,5-dimethyl-cyclohexenone oxime to 3,5-dimethylaniline by catalytic reaction on palladium/carbon in triethylbenzene as solvent failed.

There has now been found a process for the preparation of 3,5-dimethylaniline which comprises passing 3,5-dimethyl-cyclohexenone oxime in the gaseous phase at temperatures of from 200° to 500° C. over a catalyst containing at least one noble metal of the 8th subgroup of the Periodic Table.

3,5-Dimethyl-cyclohexenone oxime can be prepared in the following manner (German Offenlegungsschrift No. 2,654,850; Ann. 281, 104 (1894)):

used catalysts containing ruthenium, rhodium, palladium, iridium or platinum or mixtures thereof; palladium, platinum or palladium/platinum being preferred.

Normally, carrier catalysts, for example on carbon, $SiO_2$, $Al_2O_3$, alumosilicates, spinels, chromium oxide/aluminum oxide, or zeolites as carriers, are employed. The concentration of the noble metal on the carrier is generally from 0.05 to 10, preferably 0.2 to 5, and especially 0.3 to 2.5, weight %, each relative to the weight of the carrier. The noble metals are applied to the carrier as compounds, and preferably reduced before starting the reaction, for example by passing hydrogen over them.

The catalyst may be arranged in the form of a solid bed, moving bed or fluidized bed.

The reaction temperature is generally from 200° to 500° C., preferably 250° to 400° C., and especially 270° to 380° C.

The reaction is usually carried out under reduced pressure of down to about 10 mbar, or under normal pressure; elevated pressure of up to about 20 bars, however, being possible. Preferably, a carrier gas is used for the transport of the oxime over the catalyst. Suitable carrier gases are particularly hydrogen, nitrogen, $NH_3$, argon, $CO_2$, methane, steam, ethylene or propylene.

Before the reaction, the oxime may be diluted with readily volatile solvents such as hydrocarbons, ethers, especially glycol and polyglycol dialkyl ethers, or water.

The following Example illustrates the invention. The liter amounts of $N_2$ and $H_2$ are relative to the standard (0° C., 1.013 bar).

EXAMPLE

In a glass reactor having a diameter of 18 mm and a length of 40 cm, there were arranged from top to bottom first a glass ball layer having a thickness of 5 cm, immediately thereafter a catalyst layer having a thickness of 16 cm and consisting of 1 weight % of Pd on $SiO_2$ balls. In a $N_2$ current, the reactor was heated to 300° C., subsequently activated for 2 hours at 280° C. with 24 l/h of nitrogen and 6 l/h of hydrogen. Thereafter, 200 g of a mixture of 162 g of dimethyl-diglycol and 38 g of 3,5-dimethyl-cyclohexen-2-one-oxime-1 and simultaneously 80 l of nitrogen and 56 l of hydrogen were passed within 4 hours from above over the catalyst heated at 280° C. by means of an electric heater.

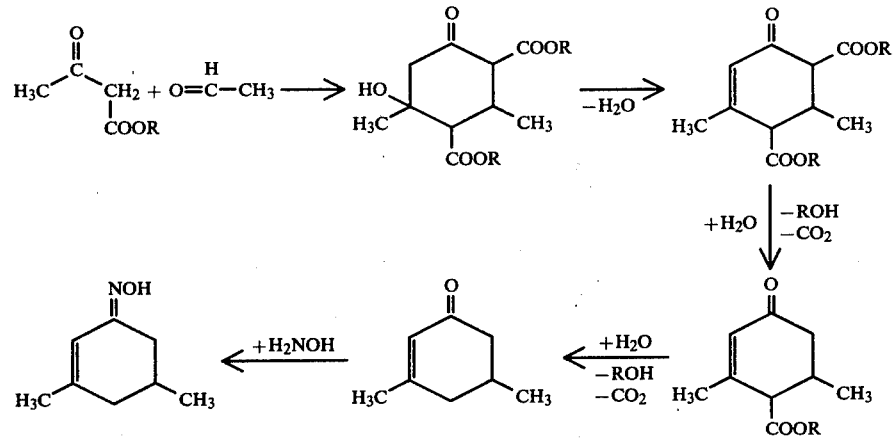

For the reaction of 3,5-dimethyl-cyclohexenone oxime according to the invention, there are generally 184.4 g of product were condensed at the reactor outlet. Gas chromatography analysis had the following result: 26.1 g of 3,5-dimethylaniline corresponding to 79% of theory, and 3.5 g of dixylylamine ≙ 11.4% of theory.

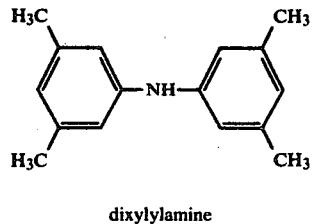

dixylylamine

After having distilled off the dimethyl-diglycol, pure 3,5-dimethylaniline was obtained by distillation under reduced pressure.

What is claimed is:

1. A process for the preparation of 3,5-dimethylaniline which comprises passing 3,5-dimethyl-cyclohexenone oxime in the gaseous phase at temperatures of from 200° to 500° C. over a catalyst containing at least one noble metal of the 8th subgroup of the Periodic Table.

2. The process as claimed in claim 1, which comprises using palladium or platinum or mixtures thereof as noble metal.

3. The process as claimed in claim 1 or 2, which comprises operating at temperatures of from 270° to 380° C.